United States Patent [19]

Hendrickx

[11] 4,300,001
[45] Nov. 10, 1981

[54] DESENSITIZED TNT; ITS PREPARATION AND USE

[75] Inventor: Andreas J. J. Hendrickx, Venlo, Netherlands

[73] Assignee: Océ-Andeno B.V., Venlo, Netherlands

[21] Appl. No.: 121,838

[22] Filed: Feb. 15, 1980

[30] Foreign Application Priority Data

Feb. 21, 1979 [NL] Netherlands ............. 7901342

[51] Int. Cl.³ ............ C06B 25/04; C06B 49/00; C06B 37/10; C07C 79/10
[52] U.S. Cl. ................... 568/767; 568/319; 568/356; 568/376; 568/771; 568/935; 568/925
[58] Field of Search ........... 568/935, 771, 767, 319, 568/356, 376, 925

[56] References Cited

U.S. PATENT DOCUMENTS

| | | | |
|---|---|---|---|
| 2,126,162 | 8/1938 | Wyler | 568/935 |
| 2,475,095 | 7/1949 | Hoek | 568/935 |
| 3,000,972 | 9/1961 | Bonetti | 568/935 |
| 3,799,993 | 3/1974 | Hill et al. | 568/935 |

FOREIGN PATENT DOCUMENTS

| | | |
|---|---|---|
| 2308430 | 8/1974 | Fed. Rep. of Germany . |
| 2349640 | 4/1975 | Fed. Rep. of Germany . |
| 863154 | 12/1940 | France . |
| 2102642 | 4/1972 | France . |
| 2102815 | 4/1972 | France . |
| 18281 | of 1910 | United Kingdom ............. 568/935 |

OTHER PUBLICATIONS

Kastens et al., Industrial and Engineering Chemistry, vol. 42, pp. 402 to 403 (1950).
Urbanski, Chemistry and Technology of Explosives, vol. 1, The MacMillan Co., N. Y., 1964, pp. 290 to 293 and 341 (TP270U7).
Lange's Handbook of Chemistry, Handbook Publishers, Inc., Sandasky, Ohio, 1946, pp. 1319 to 1324 (TP151H25).
The Condensed Chemical Dictionary, 9th Ed., Van Nostrand Reinhold Co., 1977, p. 827 (PD5C5).

*Primary Examiner*—Teddy S. Gron
*Attorney, Agent, or Firm*—Albert C. Johnston

[57] ABSTRACT

The explosive 2,4,6-trinitrotoluene (TNT) is desensitized by dissolving it in oleum of from 10 to 40% (by weight) in strength. The solutions formed preferably contain at least 400 g and at most 480 g of dissolved TNT per liter of oleum in oleum of 20-25% strength. They are especially useful for the preparation of phloroglucinol.

9 Claims, No Drawings

DESENSITIZED TNT; ITS PREPARATION AND USE

The present invention relates to a process for desensitizing the explosive 2,4,6-trinitrotoluene, hereinafter referred to by the abbreviation TNT. The invention relates also to resultant insensitive solutions of TNT and to their use for the preparation of phloroglucinol.

By desensitizing as used herein is meant minimization of the sensitivity of an explosive compound to heat and shock without depriving the compound of its explosive property. The purpose of desensitization is to enable safer handling of the explosive compound.

Certain processes for the desensitization of explosive compounds, especially of high-explosives, are already known. For example, Urbanski and Galas, in C.r. 209 (1939) 558, disclose the addition to such compounds of non-explosive liquids such as chloroform, n-heptane, acetone, $H_2O$ and glycerin. French Pat. No. 863 154 discloses that the shock sensitivity of explosive compounds, including TNT, can be diminished by mixing or enveloping the explosive compound with a waxy or fatty material, such as paraffin wax or a stereate. French Pat. Nos. 2 102 642 and 2 102 815 describe a process of desensitization in which the explosive compound in granular form is enveloped with a layer of natural or synthetic wax of which the melting point preferably is in the range between 60° and 72° C.

Further, a German patent application No. 2 308 430 laid open for public inspection describes a method of desensitizing in which grains of the high-explosive substance are coated with a layer of wax and then the coated grains are dried and subsequently tempered.

Another German patent application laid open for public inspection, No. 2 349 640, cites mono-, di- and trinitro-derivatives of benzene, toluene, xylene, etc. as examples of desensitizing agents for gelatinous explosive compounds. In other words, TNT itself is there proposed as a desensitizing agent.

All the above-mentioned known methods of desensitization have the disadvantage that the desensitizing effect is insufficient, as will be further demonstrated hereinbelow.

Moreover, those known methods relate to utilization of the desensitized compound as an explosive, in which case the presence or envelopment of the explosive with a comparatively small amount of an inert substance is not particularly objectionable. In the case, however, of TNT being used as a starting material for the preparation of phloroglucinol, the presence of or envelopment of the TNT with inert substances, such as a layer of wax, is highly objectionable, because these substances must be removed before the TNT is so used. Also, the desensitizing effect is lost when they are removed.

The principal object of the present invention is to provide a process for desensitizing TNT that does not present the drawbacks mentioned above.

Other objects of the invention are to provide TNT solutions which are safely insensitive to heat and shock and are useful as a reactant chemical, and to provide a process employing such solutions for the preparation of phloroglucinol.

According to the present invention, it has been found that the explosive TNT can be desensitized advantageously by dissolving TNT in oleum of which the strength (i.e., the amount of $SO_3$ dissolved therein) is in the range from 10% to 40% by weight.

Although any amount of TNT dissolved in such oleum is desensitized, the desensitizing is of practical importance only if the solution obtained contains at least a certain minimum amount of dissolved TNT. In this regard, an amount of 80 g TNT per liter of oleum of 10% strength is considered a practical lower limit. The upper limit of the amount of TNT to be dissolved is determined by the desired degree of desensitization, for the more TNT is dissolved the more readily the TNT will crystallize out of the solution, and crystallized TNT is no longer in a desensitized state. A practical upper limit in this regard, generally speaking, amounts of about 600 g of dissolved TNT per liter of oleum of 40% strength.

The oleum to be used according to the invention advantageously is commercially available oleum containing 20 to 25% by weight of dissolved $SO_3$ (in short: oleum 20–25%). The amount of TNT to be dissolved in such oleum preferably is in the range from 320 to 500 g per liter, and more particularly, from 400 to 480 g per liter.

When a solution of 480 g of TNT per liter of oleum 20–25% is stored for 5 full days (24 hours each) at 0° C., the TNT will not crystallize out, and not even if the solution is injected with crystalline TNT. In the case of a solution of 400 g of TNT per liter of oleum 20–25%, crystallization will not occur even at −10° C. after the solution is allowed to stand for 5 full days, nor does it occur when TNT seed crystals are added to this solution.

The results of tests measuring the desensitizing effect of oleum as herein disclosed, as well as the effects of other desensitizing means, in respect of the explosiveness of TNT when subjected to shock, friction and heat, were determined by the statutory methods employed in classifying dangerous materials under regulations for the transportation of dangerous substances. Those methods are assumed to be known to those skilled in the art. The table also shows the requirements to be met by desensitized TNT in order for it to fall outside the class of hazardous explosive substances to which strict transport regulations are applicable.

TABLE

|  | Sensitivity to shock (in kgm) | Sensitivity to friction (in kgf) | Sensitivity to heat (in mm) |
| --- | --- | --- | --- |
| TNT pure | 2.4 | >36 | 5 to 8 |
| Requirements in transport regulations for dangerous substances | >5 | >36 | <1 |
| TNT/talc powder |  |  |  |
| wt/wt 80/20 | 2.5 | >36 | 4 to 6 |
| 70/30 | 3 | >36 | 2 |
| TNT/paraffin wax |  |  |  |
| wt/wt 80/20 | 3.9 | >36 | 3 |
| 70/30 | 6.3 | >36 | 1.5 |
| 60/40 | 7.3 | >36 | 2 |
| 40/60 | — | >36 | >1 |
| TNT/Nibren* wax |  |  |  |
| wt/wt 80/20 | 9.4 | >36 | 3 |
| TNT/kieselguhr |  |  |  |
| wt/wt 80/20 | — | — | 2 |
| 60/40 | 0.5 | — | 0 |
| TNT/oleum 20% 600 g/L | >120 | >36 | <1 |

*Nibren = mixture of tetrachloronapthalene

As is evident from the table, TNT desensitized with Kieselguhr can be properly desensitized in respect of its sensitivity to heat, but, on the other hand, becomes more sensitive to shock; whereas with paraffin wax the requirements can be satisfied in respect of the sensitivity to shock but not so in respect of the sensitivity to heat. The requirements in respect of both shock and heat are not met sufficiently by desensitizing TNT with any of the known means tested, namely, talc powder, paraffin wax, Nibren wax or kieselguhr.

On the other hand, as the table shows, a superb desensitizing effect is obtained with oleum. For instance, with one liter of oleum 20%, 600 g of TNT can be desensitized so that the TNT loses its nature of being a dangerous explosive compound.

TNT can also be desensitized by dissolving it in concentrated (i.e., at most 100%) sulfuric acid. This, however, has no practical value because TNT has too low a solubility in concentrated sulfuric acid, and wetting of TNT with concentrated sulfuric acid has an insufficient desensitizing effect. For example, in testing the sensitivity to heat of mixtures of 1,000 g of TNT with 250 to 1,000 ml of concentrated sulfuric acid, values exceeding 1 mm were always obtained.

In view of the fact that, in general, safety and environmental regulations are becoming more and more stringent, and particularly so for dangerous explosive compounds such as TNT, the importance of the desensitizing process herein disclosed is evident. This way of achieving desensitization has significant advantages and consequences for the storage, transportation, handling and processing of TNT. By virtue of such desensitization, TNT can now be stored in ways, and in areas and buildings, which as a rule are unacceptable for TNT as an explosive compound. For example, since the TNT is present in a dissolved state, it can be stored in tanks and pumped from them for use. In regard to transportation, when TNT is desensitized according to the invention the solution may be transported by tank car, in which case transportation of the TNT comes into another class of less dangerous materials, with all its attendant advantages.

The solutions of TNT in oleum of 10% and higher concentration are believed to be new, and are an important product of the invention in view of the advantages and results outlined above. Accordingly, the invention provides solutions of TNT in fuming sulfuric acid, which contain at least 80 g and at most 600 g of dissolved TNT per liter of oleum in oleum of 10 to 40% strength, the amount of dissolved TNT being dependent on the strength chosen for the oleum. Solutions are preferred which contain at least 320 g and at most 500 g, and more particularly 400 to 480 g, of TNT per liter of oleum in oleum of 20-25% strength.

An additional, very important advantage of the TNT solutions according to the invention is that they can be employed as such for the large-scale manufacture of phloroglucinol. Consequently, the invention also provides a process for the preparation of phloroglucinol from TNT that has been desensitized by being dissolved in fuming sulfuric acid in accordance with the invention. In this process the TNT, after dilution of the sulfuric acid medium to a concentration below 100%, is converted by oxidation into 2,4,6-trinitrobenzoic acid, which acid is then reduced to 2,4,6-triaminobenzoic acid which in turn is hydrolysed and decarboxylated.

The advantages resulting from this process of preparing phloroglucinol are many. Among them are:

eased transport of the TNT from yard to reaction vessel;

the prior dissolving of TNT in sulfuric acid is no longer necessary;

the TNT is in the desensitized state until it enters the reaction process;

saving of energy and gain of time.

The saving of energy and gain of time are realized due to the fact that the conversion by oxidation into trinitrobenzoic acid occurs in a sulfuric acid medium of lower than 100% concentration, so that the TNT solutions according to the invention must be diluted with water. The heat released in the dilution process can serve as the heat of reaction necessary for the oxidation step. In other words, the previous warming-up step can be omitted, with resultant savings of energy and time.

The following example further illustrates the practice of the invention.

EXAMPLE 250 ml of fuming sulfuric acid containing 20% by weight of $SO_3$ (oleum 20%), are set stirring while being sealed against moisture. To this liquid 100 g of TNT in the form of flakes are added in portions at room temperature. Stirring is continued until all the TNT has been dissolved.

What is claimed is:

1. A process for desensitizing the explosive 2,4,6-trinitrotoluene (TNT), which comprises dissolving TNT in oleum of from 10 to 40% (by weight) in strength.

2. A process according to claim 1, the TNT being so dissolved in an amount, depending upon the strength of the oleum, of at least 80 g and at most 600 g per liter of the oleum.

3. A process according to claim 1, the TNT being so dissolved in oleum of 20-25% strength in an amount of at least 320 g and at most 500 g of TNT per liter of the oleum.

4. A process according to claim 1, the TNT being so dissolved in oleum of 20-25% strength in an amount of at least 400 g and at most 480 g of TNT per liter of the oleum.

5. A solution of 2,4,6-trinitrotoluene (TNT) in oleum of 10 to 40% (by weight) in strength, said solution containing dissolved TNT in an amount, depending upon the strength of the oleum, of at least 80 g and at most 600 g per liter of the oleum.

6. A solution accoding to claim 5 consisting essentially of at least 320 g and at most 500 g of dissolved TNT per liter of oleum in oleum of 20-25% strength.

7. A solution according to claim 5 consisting essentially of at least 400 g and at most 480 g of dissolved TNT per liter of oleum in oleum of 20-25% strength.

8. In a process for preparing phloroglucinol from 2,4,6-trinitrotoluene (TNT), which comprises converting TNT dissolved in concentrated sulfuric acid, by oxidation, into 2,4,6-trinitrobenzoic acid, reducing the trinitrobenzoic acid to 2,4,6-triaminobenzoic acid and hydrolysing and decarboxylating the latter, the improvement which comprises supplying as the TNT starting reactant for the process a solution of TNT desensitized in oleum according to claim 1, 2, 3, or 4.

9. A process according to claim 8, and diluting said solution with water to a sulfuric acid concentration below 100% to obtain said TNT dissolved in concentrated sulfuric acid, thereby generating heat for the oxidation reaction.

* * * * *